United States Patent [19]

Fowler et al.

[11] Patent Number: 5,247,119

[45] Date of Patent: Sep. 21, 1993

[54] PHENYLACETONITRILEHYDROXYALK-YLAMINOALKYL-ORTHO-SUBSTITUTED ARYL COMPOUNDS AS IMMUNOSUPPRESSIVES

[75] Inventors: Kerry W. Fowler, Seattle, Wash.; John M. Farah, Jr., St. Louis; John P. McKearn, Pacific, both of Mo.; Richard A. Mueller, Glencoe, Ill.; Susan A. Gregory, St. Louis, Mo.

[73] Assignee: G. D. Searle & Co., Chicago, Ill.

[21] Appl. No.: 889,733

[22] Filed: May 28, 1992

Related U.S. Application Data

[63] Continuation-in-part of Ser. No. 626,158, Dec. 12, 1990, abandoned.

[51] Int. Cl.$^5$ .................. C07C 255/33; C07C 255/36; C07C 255/42; A61K 31/275
[52] U.S. Cl. ............................... 558/390; 558/408; 558/404; 558/405; 558/406; 558/407
[58] Field of Search ................ 558/390, 408; 514/653, 514/523

[56] References Cited

U.S. PATENT DOCUMENTS

| | | | |
|---|---|---|---|
| 3,261,859 | 7/1966 | Dengel . | |
| 4,115,432 | 9/1978 | Dengel | 558/390 |
| 4,350,636 | 9/1982 | Kastner et al. | 558/390 |
| 4,438,131 | 3/1984 | Ehrmann et al. | 514/523 |
| 4,593,042 | 8/1986 | Liang . | |
| 4,681,970 | 7/1987 | Liang . | |
| 4,847,403 | 7/1989 | Bláha et al. | 558/390 |
| 4,925,837 | 5/1990 | Cavero et al. | 514/523 |
| 4,968,717 | 11/1990 | Unger et al. | 514/523 |

FOREIGN PATENT DOCUMENTS

| | | | |
|---|---|---|---|
| 0066246 | 12/1982 | European Pat. Off. | 514/523 |
| 0434095 | 6/1991 | European Pat. Off. | 558/390 |
| 0276362 | 9/1967 | Fed. Rep. of Germany | 558/390 |

OTHER PUBLICATIONS

Ganellin et al., *J Chem Soc.* (C), 16, pp. 2132–2134 (1969).
G. Walz et al, *Transplantation*, 47, 331–334 (1989).
A. Nel et al, *Scand. J. Immunology*, 24, 283–290 (1986).
W. R. Chen et al, *Acta Pharmacologica Sinica*, 11(3), 281–285 *Abstract Only* (1985).

*Primary Examiner*—José G. Dees
*Assistant Examiner*—B. Frazier
*Attorney, Agent, or Firm*—J. Timothy Keane

[57] ABSTRACT

A class of substituted phenylacetonitrilehydroxyalkylaminoalkyl-ortho-substituted aryl compounds having immunosuppressive properties is described. Compounds of this class would be useful in reducing recipient rejection of transplanted organs and for treatment of autoimmune or inflammatory diseases. Compounds of particular interest are of the formula

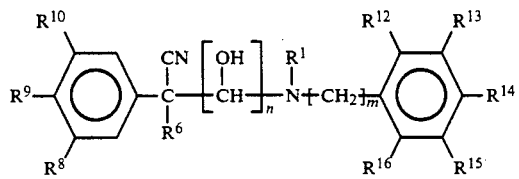

wherein each of m and n is a number independently selected from one to five, inclusive; wherein $R^1$ is selected from hydrido, alkyl, hydroxyalkyl, cycloalkyl, cycloalkylalkyl, alkoxyalkyl, alkenyl and alkynyl; wherein $R^6$ is selected from loweralkyl; wherein each of $R^8$, $R^9$, $R^{10}$ and $R^{12}$ through $R^{16}$ is independently selected from hydrido, hydroxy, alkyl, hydroxyalkyl, alkoxy, alkenyl, alkynyl, alkylcarbonyl, alkoxycarbonyl, alkylcarbonylalkenyl, alkylaminocarbonyl and alkoxyalkyl; or a tautomer thereof or a pharmaceutically-acceptable salt thereof.

10 Claims, No Drawings

PHENYLACETONITRILEHYDROXYALKYLAMINOALKYL-ORTHO-SUBSTITUTED ARYL COMPOUNDS AS IMMUNOSUPPRESSIVES

RELATED APPLICATION

This is a continuation-in-part of U.S. application Ser. No. 07/626,158 filed Dec. 12, 1990, now abandoned.

FIELD OF THE INVENTION

This invention is in the field of clinical immunology and relates to compounds having immunosuppressive properties. Of particular interest is a family of phenylacetonitrilehydroxyalkylaminoalkyl-o-substituted aryl compounds for reducing recipient rejection of transplanted organs, and for treatment of autoimmune or inflammatory diseases, allergic or asthmatic reactions and septic shock.

BACKGROUND OF THE INVENTION

Successful organ transplantation requires effective physiological and pharmacological intervention of the immune system of an organ recipient. Immunologic mechanisms are universal among the human species. But histocompatibility variations between donor and recipient lead inevitably to rejection of donor tissue by stimulation of the recipient's immune system except, perhaps, in donor-recipient pairing of the monozygotic type. One approach to intervention of immune response in an organ transplant recipient, especially a recipient targeted for an allogenic or homologous graft, is by the use of immunosuppressive drugs. These drugs have been used to prolong survival of transplanted organs in recipients in cases involving, for example, transplants of kidney, liver, heart, bone marrow and pancreas.

There are several types of immunosuppressive drugs available for use in reducing organ rejection in transplantation. Such drugs fall within three major classes, namely: antiproliferative agents, antiinflammatory-acting compounds and inhibitors of lymphocyte activation.

Examples of the class of antiproliferative agents are azathioprine, cyclophosphamide and methotrexate. The compound azathioprine acts by interrupting DNA synthesis through inhibition of purine metabolism. The compound cyclophosphamide is an alkylating agent which interferes with enzyme actions and nucleotide cross-linking. The compound methotrexate is a folic acid antagonist which interferes with nucleotide synthesis. While drugs of the antiproliferative class may be effective immunosuppressives in organ transplant recipients by limiting cell proliferation, these drugs which mediate mitosis and cell division have severe side effects on normal cell populations which have a high turn-over rate, such as bone marrow cells and cells of the gastrointestinal (GI) tract lining. Accordingly, such drugs often have severe side effects, particularly, bone marrow depression, liver damage, hair loss and GI tract disturbances.

A second class of immunosuppressive drugs for use in transplantation is provided by compounds having antiinflammatory action. Representatives of this drug class are generally known as adrenal corticosteroids and have the advantage of not exerting globally systemic cytotoxic effects. These compounds usually act by inhibiting T-cell proliferation, or by reducing IL-2 production, or by reducing chemotaxis, or by reducing neutrophil or macrophage activity. Typical examples of adrenal corticosteroids are prednisone and prednisolone. Compounds of this class are sometimes used in combination with cytotoxic agents, such as compounds of the antiproliferative class because the corticosteroids are significantly less toxic. But the adrenal corticosteroids lack specificity of effect and can exert a broad range of metabolic, antiinflammatory and auto-immune effects. Typical side effects of this class include increased organ-recipient infections and interference with wound healing, as well as disturbing hemodynamic balance, carbohydrate and bone metabolism and mineral regulation.

A third class of immunosuppressive drugs for use in organ transplantation is provided by compounds which generally prevent or inhibit lymphocyte activation. Such compounds usually act by blocking activated T-cell proliferation, or by inhibiting IL-2 production, or by inhibiting lymphokine production which depresses B-cell and macrophage actions. The cyclosporin family of compounds is the leading example of drugs in this class. Such compounds are fungal metabolites which have been found to be very effective in suppressing helper T cells so as to reduce both cellular and humoral responses to newly-encountered antigens. Cyclosporins alter macrophage and lymphocyte activity by reducing lymphokine secretion and, in particular, by interfering with activation of antigen-specific CD-4 cells, by preventing IL-2 secretion and secretion of many T-cell products, as well as by interfering with expression of receptors for these lymphokines. Cyclosporin A, in particular, has been used extensively as an immunosuppressor agent in organ transplantation. Other microbial metabolites include cyclosporins such as cyclosporin B and cyclosporin G, and another microbial product known as FK-506. Cyclosporin A suppresses humoral immunity as well as cell-mediated reactions. Cyclosporin A is indicated for organ rejection in kidney, liver, heart, pancreas, bone-marrow and heart-lung transplants. Cyclosporin A is also useful in the treatment of autoimmune and inflammatory diseases, including rheumatoid arthritis, Crohn's disease, Graves opthalmopathy, severe psoriasis, aplastic anemia, multiple-sclerosis, alopecia areata, penphigus and penphigoid, dermatomyositis, polymyositis, Behcet's disease, uveitis, pulmonary sarcocidiosis, biliary cirrhosis, myasthenia gravis and atopic dermatitis.

Cyclosporins do possess several significant disadvantages. Firstly, while cyclosporins have provided significant benefits in organ transplantation, cyclosporins are non-specific immunosuppressives. Thus, immunologic reactions to transplanted tissue are not totally impeded, and desirable immune reactions may be reduced against other foreign antigens. Secondly, cyclosporins can produce severe side effects in many organ recipients. And cyclosporins show host-variable effects on the liver, the CNS and GI tract. Significant among the adverse side effects are damage to the kidney and hyperplasia of gum tissue.

Thus, the need remains for efficacious, selective immunosuppressive drugs in organ transplantation, especially for grafts between less-than-perfectly matched donor-recipient pairs.

Phenylacetonitrile compounds are known for use in treatment of cardiovascular diseases. For example, U.S. Pat. No. 3,261,859 describes phenylacetonitrile compounds, including the well-known compound verapamil, for use as coronary dilators. U.S. Pat. No. 4,593,042 describes certain bicycloamino-substituted phenylacetonitrilealkyl compounds, including several specific compounds having an isopropyl group attached to the alkylene alpha carbon of the phenylacetonitrile nucleus. Such compounds are characterized as calcium ion blockers for use in treatment of hypertension. U.S. Pat. No. 4,681,970 describes bicycloamino-substituted phenylacetonitrilealkyl compounds, several specific compounds of which have a long chain alkyl group (i.e., twelve carbons) attached to the alkylene alpha carbon of the phenylacetonitrile nucleus. These compounds are characterized as calcium channel blockers for treatment of hypertension.

Phenylacetonitrile compounds have been investigated for other pharmaceutical purposes. For example, certain calcium channel blocking agents, including verapamil, have been investigated for antiproliferative effects on T-cell mitogenesis [G. Walz et al, *Transplantation*, 47, 331-334 (1989)]. Various calcium channel blockers, including verapamil and nifedipine, have been studied for interaction with stimulated T-lymphocytes [A. Nell et al, *Scand. J. Immunology*, 24, 283-290 (1986)]. German Offen. 3826796 published Feb. 8, 1990 describes substituted phenylacetonitrile compounds for use in overcoming resistance to antimalarial or anticancer agents. The calcium antagonists verapamil, nifedipine and nicardipine were compared and found to produce dose-dependent acute and chronic antiinflammatory effects [W. R. Chen et al, *Acta. Pharmacologica Sinica*, 11 (3), 281-285 (1990)].

DESCRIPTION OF INVENTION

Reduction in recipient rejection of a transplanted organ, or treatment of an autoimmune or inflammatory disease, or an allergic reaction or asthmatic condition, or treatment of septic shock may be accomplished by a method to suppress immune response in a recipient or treatment subject, which method comprises administering to the subject a therapeutically-effective amount of an immunosuppressive compound of Formula I:

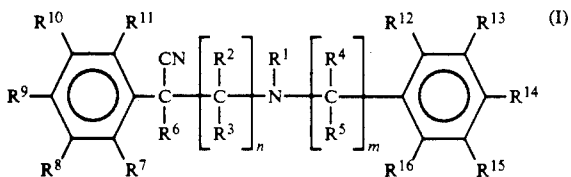

wherein each of m and n is a number independently selected from one to ten, inclusive; wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkylaryloxycarbonylalkyl, alkenyl, cycloalkenyl, aralkoxycarbonylalkyl, alkynyl, alkylthiocarbonylalkyl, alkylthiothiocarbonylalkyl, arylthiocarbonylalkyl, arylthiothiocarbonylalkyl, aralkylthiocarbonylalkyl, alkylarylthiocarbonylalkyl, alkylsulfonyl, aralkylsulfonyl and arylsulfonyl;

Wherein each of $R^2$ through $R^5$ and $R^7$ through $R^{16}$ is independently selected from hydrido, hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonylalkyl, aralkylthiocarbonylthio, mercapto, alkylsulfinyl, alkylsulfonyl, aralkylsulfinyl, aralkylsulfonyl, arylsulfinyl, arylsulfonyl, and wherein each of $R^2$ through $R^5$ and $R^7$ through $R^{16}$ may be further independently selected from radicals of the formula

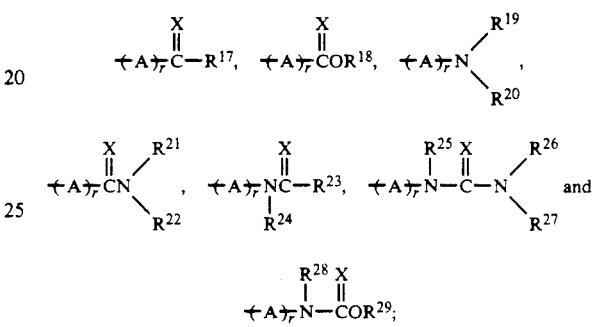

wherein A is selected from divalent alkyl, alkenyl and alkynyl groups; wherein X is oxygen atom or sulfur atom; wherein each r is a number independently selected from zero to six, inclusive; wherein each of $R^{17}$ through $R^{29}$ is independently selected from hydrido, alkyl, cycloalkyl, cycloalkylalkyl, aralkyl and aryl;

with the proviso that one of $R^2$ and $R^3$ is selected from hydroxy, cycloalkyloxy, formyl, alkoxy, aralkoxy, alkylcarbonyloxy, alkoxycarbonyloxy, alkylthio, cycloalkylthio, alkylcarbonylthio, alkylthiocarbonyloxy, alkylthiocarbonylthio, alkylthiothiocarbonylthio, arylthio, arylcarbonylthio, arylthiocarbonyloxy, arylthiocarbonylthio, arylthiothiocarbonylthio, aralkylthio, aralkylcarbonylthio, aralkylthiocarbonyloxy, aralkylthiocarbonylthio, mercapto, alkylsulfinyl, alkylsulfonyl, aralkylsulfinyl, aralkylsulfonyl, arylsulfinyl and arylsulfonyl;

wherein $R^6$ is selected from hydrido, alkyl, hydroxyalkyl, cycloalkyl, cycloalkylalkyl, cycloalkyloxy, alkoxy, aralkyl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonylalkyl, aralkylthiocarbonylthio, alkylsulfinyl, alkylsulfonyl, aralkylsulfinyl, aralkylsulfonyl, arylsulfinyl and arylsulfonyl;

and wherein any of the foregoing A and $R^1$ through $R^{29}$ groups having a substitutable position may be substituted by one or more groups independently selected from alkyl, alkenyl, alkynyl, aralkyl, hydroxy, hydroxyalkyl, cyano, alkoxyalkyl, cycloalkyl, cycloalkylalkyl, aryl, aroylalkyl, cycloalkenyl, cyanoamino, alkylcarbonylalkyl, alkoxycarbonylalkyl, aralkoxycarbonylalkyl, carboxylalkyl, alkylthiocarbonylalkyl and alkylsulfonylslkyl;

or a tautomer thereof or a pharmaceutically-acceptable salt thereof.

A preferred class consists of compounds within Formula I wherein each of m and n is a number independently selected from one to nine, inclusive;

wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkylaryloxycarbonylalkyl, alkenyl, cycloalkenyl, aralkoxycarbonylalkyl and alkynyl;

wherein each of $R^2$ through $R^5$ and $R^7$ through $R^{16}$ is independently selected from hydrido, hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonylalkyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, arylthio, mercapto, and wherein each of $R^2$ through $R^5$ and $R^7$ through $R^{16}$ may be further independently selected from radicals of the formula

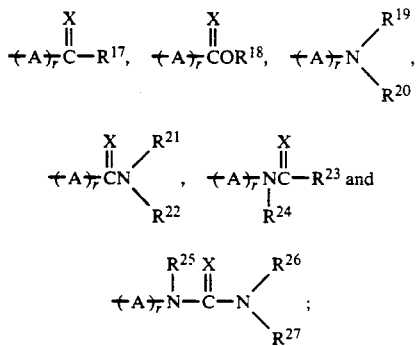

wherein A is selected from divalent alkyl, alkenyl and alkynyl groups; wherein X is oxygen atom or sulfur atom; wherein each r is a number independently selected from zero to five, inclusive; wherein each of $R^{17}$ through $R^{27}$ is independently selected from hydrido, alkyl, cycloalkyl, cycloalkylalkyl, aralkyl and aryl;

with the proviso that one of $R^2$ and $R^3$ is selected from hydroxy, cycloalkyloxy, formyl, alkoxy, aralkoxy, alkylcarbonyloxy, alkoxycarbonyloxy, alkylthio, cycloalkylthio, alkylcarbonylthio, alkylthiocarbonyloxy, alkylthiocarbonylthio, alkylthiothiocarbonylthio, arylthio, arylcarbonylthio, arylthiocarbonyloxy, arylthiocarbonylthio, arylthiothiocarbonylthio, aralkylthio, aralkylcarbonylthio and mercapto;

wherein $R^6$ is selected from hydride, alkyl, hydroxyalkyl, cycloalkyl, cycloalkylalkyl, cycloalkyloxy, alkoxy, aralkyl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptoalkyl, alkoxycarbonyloxy, alkylthio, cycloalkylthio, and wherein any of the foregoing A and $R^1$ through $R^{27}$ groups having a substitutable position may be substituted by one or more groups independently selected from alkyl, alkenyl, alkynyl, hydroxy, aralkyl, hydroxyalkyl, cyano, alkoxyalkyl, cycloalkyl, cycloalkylalkyl, aryl, aroylalkyl, cycloalkenyl, cyanoamino, alkylcarbonylalkyl, alkoxycarbonylalkyl, aralkoxycarbonylalkyl and carboxylalkyl;

or a tautomer thereof or a pharmaceutically-acceptable salt thereof.

A more preferred class consists of compounds within Formula I wherein each of m and n is a number independently selected from one to eight, inclusive;

wherein $R^1$ is selected from hydrido, alkyl, hydroxyalkyl, cycloalkyl, cycloalkylalkyl, aralkyl, aryl, aroylalkyl, alkoxyalkyl, alkylcarbonylalkyl, alkoxycarbonylalkyl, alkenyl and alkynyl, wherein each of $R^2$ through $R^5$ and $R^7$ through $R^{16}$ is independently selected from hydrido, hydroxy, alkyl, hydroxyalkyl, cycloalkyl, cycloalkylalkyl, cycloalkyloxy, formyl, alkoxy, aralkyl, aryl, aroyl, aryloxy, aryloxyalkyl, aralkoxy, alkoxyalkyl, alkylcarbonylalkyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkoxycarbonyloxy, and wherein each of $R^2$ through $R^5$ and $R^7$ through $R^{16}$ may be further independently selected from radicals of the formula

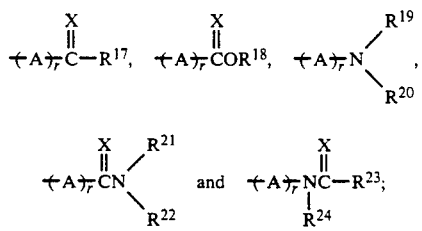

wherein A is selected from divalent alkyl, alkenyl and alkynyl groups; wherein X is oxygen atom or sulfur atom; wherein each r is a number independently selected from zero to four, inclusive; wherein each of $R^{17}$ through $R^{24}$ is independently selected from hydrido, alkyl, cycloalkyl, cycloalkylalkyl, aralkyl and aryl;

with the proviso that one of $R^2$ and $R^3$ is selected from hydroxy, cycloalkyloxy, formyl, alkoxy, alkylcarbonyloxy, alkoxycarbonyloxy, alkylthio, cycloalkylthio, alkylcarbonylthio, alkylthiocarbonyloxy, arylthio and mercapto;

wherein $R^6$ is selected from hydrido, alkyl, hydroxyalkyl, cycloalkyl, cycloalkylalkyl, cycloalkyloxy, alkoxy, aralkyl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptoalkyl, and alkoxycarbonyloxy;

and wherein any of the foregoing A and $R^1$ through $R^{24}$ groups having a substitutable position may be substituted by one or more groups independently selected from alkyl, alkenyl, alkynyl, hydroxy, aralkyl, hydroxyalkyl, cyano, alkoxyalkyl, cycloalkyl, cycloalkylalkyl, aryl, aroylalkyl, cyanoamino, alkylcarbonylalkyl, alkoxycarbonylalkyl, aralkoxycarbonylalkyl and carboxylalkyl; or a tautomer thereof or a pharmaceutically acceptable salt thereof.

An even more preferred class consists of compounds within Formula I wherein each of m and n is a number independently selected from one to seven, inclusive; wherein $R^1$ is selected from hydrido, alkyl, hydroxyalkyl, cycloalkyl, cycloalkylalkyl, alkoxyalkyl, alkylcarbonylalkyl, alkoxycarbonylalkyl, alkenyl and alkynyl; wherein each of $R^2$ through $R^5$ and $R^7$ through $R^{16}$ is independently selected from hydrido, hydroxy, alkyl, hydroxyalkyl, cycloalkyl, cycloalkylalkyl, cycloalkyloxy, alkoxy, phenylalkyl, phenyl, benzoyl, phenoxy, phenoxyalkyl, alkoxyalkyl, alkylcarbonylalkyl, alkynyl, carboxyl, carboxyalkyl, alkylcarbonyloxy, alkylcarbonyloxyalkyl, alkoxycarbonylalkyl, alkoxycarbonyloxy, and wherein each of $R^2$ through $R^5$ and $R^7$ through $R^{16}$ may be further independently selected from radicals of the formula

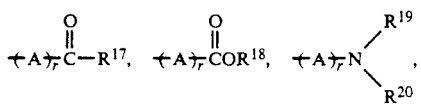

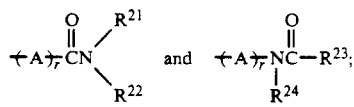

wherein A is selected from divalent alkyl, alkenyl and alkynyl groups; wherein each r is a number independently selected from zero to four, inclusive; wherein each of $R^{17}$ through $R^{24}$ is independently selected from hydrido, alkyl, cycloalkyl, cycloalkylalkyl, phenylalkyl and phenyl; with the proviso that one of $R^2$ and $R^3$ is selected from hydroxy, cycloalkyloxy, formyl, alkoxy, alkylcarbonyloxy, alkoxycarbonyloxy, alkylthio, cycloalkylthio, alkylcarbonylthio, alkylthiocarbonyloxy, phenylthio and mercapto; wherein $R^6$ is selected from hydrido, alkyl, hydroxyalkyl, cycloalkyl, cycloalkylalkyl, cycloalkyloxy, alkoxy, phenylalkyl, benzoyl, phenoxy, phenoxyalkyl, phenalkoxy, alkoxyalkyl, alkylcarbonyl, alkylcarbonylalkyl, alkoxycarbonyl, alkenyl, alkynyl, carboxyl, carboxyalkyl, alkylcarbonyloxy, alkylcarbonyloxyalkyl, alkoxycarbonylalkyl, mercaptoalkyl and alkoxycarbonyloxy; and wherein any of the foregoing A and $R^1$ through $R^{24}$ groups having a substitutable position may be substituted by one or more groups independently selected from alkyl, alkenyl, alkynyl, hydroxy, phenylalkyl, hydroxyalkyl, cyano, alkoxyalkyl, cycloalkyl, cycloalkylalkyl, phenyl, alkylcarbonylalkyl, alkoxycarbonylalkyl and carboxylalkyl; or a tautomer thereof or a pharmaceutically-acceptable salt thereof.

A more highly preferred class consists of compounds within Formula I selected from compounds of Formula II:

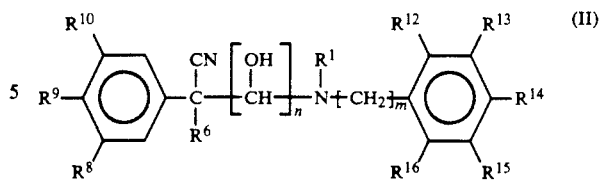

wherein each of m and n is a number independently selected from one to six, inclusive; wherein $R^1$ is selected from hydrido, alkyl, hydroxyalkyl, cycloalkyl, cycloalkylalkyl, alkoxyalkyl, alkenyl and alkynyl; wherein each of $R^8$, $R^9$, $R^{10}$ and $R^{12}$ through $R^{16}$ is independently selected from hydrido, hydroxy, alkyl, hydroxyalkyl, cycloalkyl, cycloalkylalkyl, cycloalkyloxy, alkoxy, phenoxy, benzyloxy, and radicals of the formula

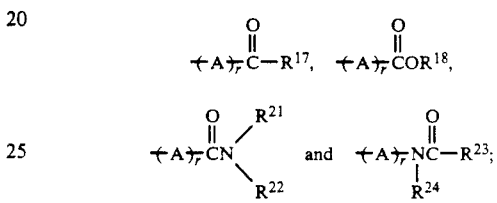

wherein A is a spacer group independently selected from one or more groups of the formula

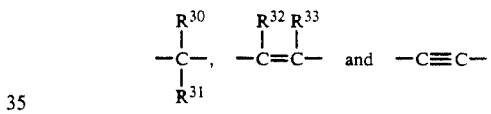

wherein each of $R^{30}$ and $R^{31}$ is independently selected from hydrido, alkyl, cycloalkyl, phenyl, benzyl, hydroxy, hydroxyalkyl, alkoxy, phenoxy, alkoxyalkyl, benzyloxy, cyano, alkanoyl,

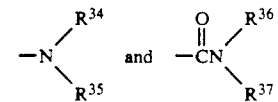

wherein each of $R^{34}$, $R^{35}$, $R^{36}$ and $R^{37}$ is independently selected from hydrido, alkyl and phenyl; wherein $R^{30}$ and $R^{31}$ may be taken together to form oxo or exomethylene; wherein each of $R^{32}$ and $R^{33}$ is independently selected from hydrido, alkyl, hydroxyalkyl and alkoxyalkyl; wherein each of $R^{17}$, $R^{18}$, $R^{19}$, $R^{20}$, $R^{21}$, $R^{22}$, $R^{23}$ and $R^{24}$ is independently selected from hydrido, alkyl, cycloalkyl, cycloalkylalkyl and phenalkyl; wherein each r is a number independently selected from zero to four, inclusive; wherein $R^6$ is selected from hydrido, alkyl, hydroxyalkyl, cycloalkyl, cycloalkylalkyl, benzyl, alkenyl and alkynyl; and wherein any of the foregoing A and $R^1$, $R^6$, $R^8$, $R^9$, $R^{10}$, $R^{12}$ through $R^{24}$ and $R^{30}$ through $R^{37}$ groups having a substitutable position may be substituted by one or more groups independently selected from alkyl, alkenyl, alkynyl, hydroxy, benzyl, hydroxyalkyl, alkoxyalkyl, cycloalkyl, cycloalkylalkyl and phenyl; or a tautomer thereof or a pharmaceutically-acceptable salt thereof.

A highly preferred class of compounds within Formula II consists of a family of compounds wherein m is one or two; wherein n is a number selected from one to five, inclusive; wherein $R^1$ is selected from hydrido, alkyl, hydroxyalkyl, alkoxyalkyl, alkenyl and alkynyl; wherein each of $R^8$, $R^9$, $R^{10}$ and $R^{12}$ through $R^{16}$ is independently selected from hydrido, hydroxy, alkyl, hydroxyalkyl, alkoxy, and radicals of the formula $$-(A)_r-\overset{O}{\overset{\|}{C}}-R^{17}, \quad -(A)_r-\overset{O}{\overset{\|}{C}}OR^{18} \quad \text{and} \quad -(A)_r-\overset{O}{\overset{\|}{C}}N\overset{R^{21}}{\underset{R^{22}}{\diagup}} ;$$

wherein A is a spacer group independently selected from one or more groups of the formula $$-\underset{R^{31}}{\overset{R^{30}}{\underset{|}{C}}}-, \quad -\underset{|}{\overset{R^{32}}{C}}=\underset{|}{\overset{R^{33}}{C}}- \quad \text{and} \quad -C\equiv C-$$

wherein each of $R^{30}$ and $R^{31}$ is independently selected from hydrido, alkyl, cycloalkyl, phenyl, benzyl, hydroxy, hydroxyalkyl, alkoxy and alkoxy and alkoxyalkyl;

wherein each of $R^{32}$ and $R^{33}$ is independently selected from hydrido, alkyl, hydroxyalkyl and alkoxyalkyl;

wherein each of $R^{17}$, $R^{18}$, $R^{21}$ and $R^{22}$ is independently selected from hydrido and alkyl;

wherein each r is a number independently selected from zero to four, inclusive;

wherein $R^6$ is selected from hydrido, alkyl, hydroxyalkyl, cycloalkyl, cycloalkylalkyl, benzyl, alkenyl and alkynyl;

and wherein any of the foregoing A and $R^1$, $R^6$, $R^8$, $R^9$, $R^{10}$, $R^{12}$ through $R^{18}$, $R^{21}$, $R^{22}$ and $R^{30}$ through $R^{33}$ groups having a substitutable position may be substituted by one or more groups independently selected from alkyl, alkenyl, alkynyl, hydroxy, hydroxyalkyl and alkoxyalkyl;

or a tautomer thereof or a pharmaceutically-acceptable salt thereof.

An even more highly preferred class of compounds within Formula II consists of a family of compounds wherein m is one or two; wherein n is a number selected from one to five, inclusive; wherein $R^1$ is selected from hydrido, alkyl, hydroxyalkyl, cycloalkyl, cycloalkylalkyl, alkoxyalkyl, alkenyl and alkynyl; wherein $R^6$ is selected from loweralkyl; wherein each of $R^8$, $R^9$, $R^{10}$ and $R^{12}$ through $R^{16}$ is independently selected from hydrido, hydroxy, alkyl, hydroxyalkyl, alkoxy, alkenyl, alkynyl, alkylcarbonyl, alkoxycarbonyl, alkylcarbonylalkenyl, alkylaminocarbonyl and alkoxyalkyl; or a tautomer thereof or a pharmaceutically-acceptable salt thereof.

A family of compounds of specific interest within Formula I consists of compounds and pharmaceutically-acceptable salts thereof, as follows:

methyl 2-[2-[[2-hydroxy-4-cyano-4-(3,4-dimethoxyphenyl)-5-methylhexyl]methylamino]ethyl]-4,5-dimethoxybenzoate;

ethyl 2-[2-[[2-hydroxy-4-cyano-4-(3,4-dimethoxyphenyl)-5-methylhexyl]methylamino]ethyl]-4,5-dimethoxybenzoate;

n-propyl 2-[2-[[2-hydroxy-4-cyano-4-(3,4-dimethoxyphenyl)-5-methylhexyl]methylamino]ethyl]-4,5-dimethoxybenzoate;

n-butyl 2-[2-[[2-hydroxy-4-cyano-4-(3,4-dimethoxyphenyl)-5-methylhexyl]methylamino]ethyl]-4,5-dimethoxybenzoate;

n-hexyl 2-[2-[[2-hydroxy-4-cyano-4-(3,4-dimethoxyphenyl)-5-methylhexyl]methylamino]ethyl]-4,5-dimethoxybenzoate;

2-[2-[[2-hydroxy-4-cyano-4-(3,4-dimethoxyphenyl)-5-methylhexyl]methylamino]ethyl]-N-(1,1-dimethylethyl)-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-methyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-ethyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-propyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-butyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-pentyl-4,5-dimethoxybenzamide;

2-[2-[[2-hydroxy-4-cyano-4-(3,4-dimethoxyphenyl)-5-methylhexyl]methylamino]ethyl]-N-ethyl-4,5-dimethoxybenzamide;

2-[2-[[2-hydroxy-4-cyano-4-(3,4-dimethoxyphenyl)-5-methylhexyl]methylamino]ethyl]-N-methyl-4,5-dimethoxybenzamide;

2-[2-[[2-hydroxy-4-cyano-4-(3,4-dimethoxyphenyl)-5-methylhexyl]methylamino]ethyl]-N-propyl-4,5-dimethoxybenzamide;

2-[2-[[2-hydroxy-4-cyano-4-(3,4-dimethoxyphenyl)-5-methylhexyl]methylamino]ethyl]-N-butyl-4,5-dimethoxybenzamide;

2-[2-[[2-hydroxy-4-cyano-4-(3,4-dimethoxyphenyl)-5-methylhexyl]methylamino]ethyl]-N-pentyl-4,5-dimethoxybenzamide;

α-[3-[[2-(4,5-dimethoxy-2-methylphenyl)ethyl]methylamino]-2-hydroxypropyl]-3,4-dimethoxy-α-(1-methylethyl)benzeneacetonitrile;

α-[3-[[2-(4,5-dimethoxy-2-ethylphenyl)ethyl]methylamino]-2-hydroxypropyl]-3,4-dimethoxy-α-(1-methylethyl)benzeneacetonitrile;

α-[3-[[2-(4,5-dimethoxy-2-propylphenyl)ethyl]methylamino]-2-hydroxypropyl]-3,4-dimethoxy-α-(1-methylethyl)benzeneacetonitrile;

α-[3-[[2-(4,5-dimethoxy-2-butylphenyl)ethyl]methylamino]-2-hydroxypropyl]-3,4-dimethoxy-α-(1-methylethyl)benzeneacetonitrile;

α-[3-[[2-(4,5-dimethoxy-2-pentylphenyl)ethyl]methylamino]-2-hydroxypropyl]-3,4-dimethoxy-α-(1-methylethyl)benzeneacetonitrile;

α-[3-[[2-(4,5-dimethoxy-2-methylphenyl)ethyl]methylamino]-2-hydroxypropyl]-3,4,5-trimethoxy-α-(1-methylethyl)benzeneacetonitrile;

α-[3-[[2-(4,5-dimethoxy-2-ethylphenyl)ethyl]methylamino]-2-hydroxypropyl]-3,4,5-trimethoxy-α-(1-methylethyl)benzeneacetonitrile;

α-[3-[[2-(4,5-dimethoxy-2-propylphenyl)ethyl]methylamino]-2-hydroxypropyl]-3,4,5-trimethoxy-α-(1-methylethyl)benzeneacetonitrile;

α-[3-[[2-(4,5-dimethoxy-2-butylphenyl)ethyl]methylamino]-2-hydroxypropyl]-3,4,5-trimethoxy-α-(1-methylethyl)benzeneacetonitrile;

α-[3-[[2-(4,5-dimethoxy-2-pentylphenyl)ethyl]methylamino]-2-hydroxypropyl]-3,4,5-trimethoxy-α-(1-methylethyl)benzeneacetonitrile;

α-[3-[[2-[4,5-dimethoxy-2-(3-oxo-1E-butenyl)phenyl]ethyl]methylamino]2-hydroxypropyl]-3,4-dimethoxy-α-(1-methylethyl)benzeneacetonitrile;

α-[3-[[2-[4,5-dimethoxy-2-(3-oxo-1E-pentenyl)phenyl]ethyl]methylamino]2-hydroxypropyl]-3,4-dimethoxy-α-(1-methylethyl)benzeneacetonitrile;

α-[3-[[2-[4,5-dimethoxy-2-(3-oxo-1E-butanyl)phenyl]ethyl]methylamino]2-hydroxypropyl]-3,4-dimethoxy-α-(1-methylethyl)benzeneacetonitrile;

α-[3-[[2-[2-(hydroxymethyl)-4,5-dimethoxyphenyl]ethyl]methylamino]2-hydroxypropyl]-3,4-dimethoxy-α-(1-methylethyl)benzeneacetonitrile; and 1-methylethyl 2-[2-[[2-hydroxy-4-cyano-4-(3,4-dimethoxyphenyl)-5-methylhexyl]methylamino]ethyl]-4,5-dimethoxybenzoate.

The term "hydrido" denotes a single hydrogen atom (H). This hydrido group may be attached, for example, to a oxygen atom to form a hydroxyl group; or, as another example, two hydrido groups may be attached to a carbon atom to form a —CH$_2$— group. Where the term "alkyl" is used, either alone or within other terms such as "hydroxyalkyl", the term "alkyl" embraces linear or branched radicals having one to about twenty carbon atoms or, preferably, one to about fifteen carbon atoms. For some substituents, more preferred alkyl radicals are "lower alkyl", that is, radicals having one to about ten carbon atoms. For some substituents, most preferred alkyl radicals are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The term "alkylthio" embraces radicals containing a linear or branched alkyl group, of one to about ten carbon atom attached to a divalent sulfur atom, such as a methylthio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote, respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and SO$_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more preferred sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroalkyl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl, neopentyl, n-hexyl, n-heptyl, n-octyl, n-nonyl, n-decyl, n-undecyl, n-dodecyl, n-tridecyl, n-tetradecyl and n-hexadecyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

It is preferred that certain selections of radicals for $R^1$ be avoided. Radicals for $R^1$ which should preferably be avoided are alkyl, alkenyl and alkynyl moieties having a hydroxy, alkoxy or double or triple bond attached to the alpha carbon of the moiety, that is, the carbon attached to the nitrogen atom of Formula I on which $R^1$ is substituted. It is also preferred that certain selections of radicals for $R^6$ be avoided. Radicals for $R^4$ which should preferably be avoided are sulfhydryl, amino and mono- and di-substituted amino.

Also included in the family of compounds of Formulas I are isomeric forms including diastereoisomers, regioisomers and the pharmaceutically-acceptable salts thereof. The term "pharmaceutically-acceptable salts" embraces salts commonly used to form alkali metal salts and to form addition salts of free acids or free bases, including quaternary ammonium salts. The nature of the salt is not critical, provided that it is pharmaceutically-acceptable. Suitable pharmaceutically-acceptable acid addition salts of compounds of Formulas I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formulas I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

GENERAL SYNTHETIC PROCEDURES

Compounds embraced by Formula I may be prepared in accordance with Scheme I, which follows, wherein each of the R substituents are as defined in Formula I above, except where further noted.

Synthesis of the compounds of Formula I can be achieved by the reaction of bis-electrophile, sequentially, with two nucleophiles (Scheme I). The bis-electrophile can be, for example, an alkyl chain, substituted at the desired positions with a halogen or a sulfonic acid ester or the like or by a group that can be transformed into such an electrophile. A second class of bis-electrophilic species is represented by a halogen or a sulfonic acid ester combined with an epoxide as the second electrophilic group, thus allowing the generation of a hydroxyl group. It may be convenient, upon treatment with a nucleophile, that the two electrophilic groups have a differential reactivity toward nucleophilic substitution, e.g., a chloro group and a bromo group. Examples of bis-electrophiles are 3-bromo-chloropropane, 4-bromo-chlorobutane, 4-bromobutane-1-paratoluenesulfonate, 1-chloro-2,3-epoxypropane, 1-bromo-4,5-epoxyhexane, 5-chloro-1-methyl-butanetrifluoromethanesulfonate and the like. Examples of nucleophiles that can be reacted with the above bis-electrophiles are the anions of aryl-propionitriles, prepared using non-nucleophilic bases, and primary or secondary amines. Non-nucleophilic bases are, for example, sodium hydride, potassium hydride, lithium di-iso-propyl amide (LDA, the salt of a sterically hindered amine) and the like. Electrophilic groups are indicated in Scheme I by $E_1$ and $E_2$.

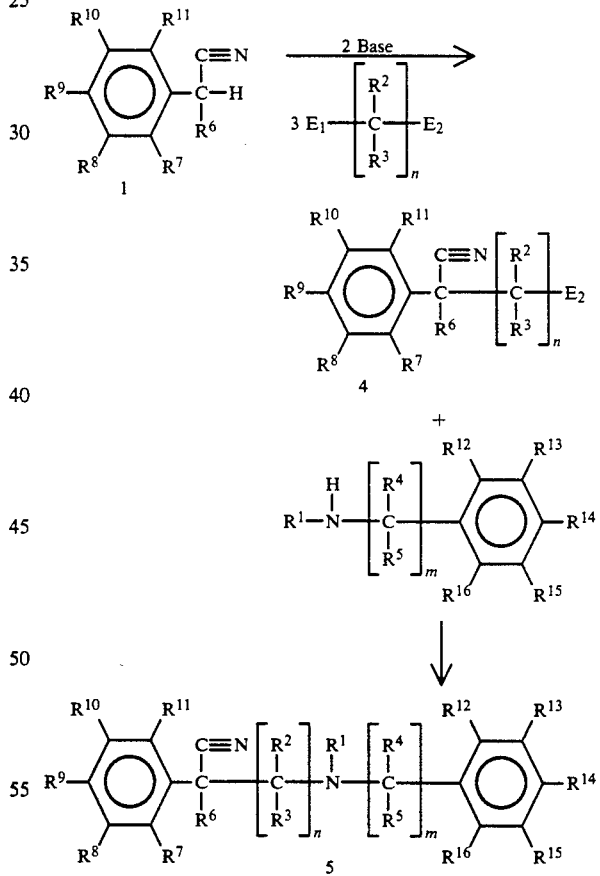

SCHEME I

The following Example 1 is a detailed description of the method of preparation of compounds of Formula I. This detailed preparation falls within the scope of, and serves to exemplify, the above described Generic Procedure which form part of the invention. This Example 1 is presented for illustrative purposes only and is not intended as a restriction on the scope of the invention. All parts are by weight unless otherwise indicated.

EXAMPLE 1

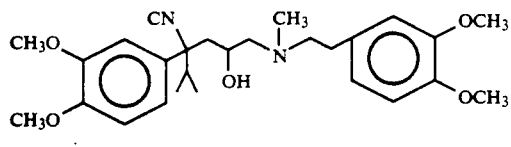

α-[3-[[2-(3,4-dimethoxyphenyl)ethyl]methylamino]-2-hydroxypropyl]-3,4-dimethoxy-α-(1-methylethyl)benzeneacetonitrile (a mixture of two racemates)

Step (a): Preparation of 1,2-epoxy-4-(3,4-dimethoxyphenyl)-4-cyano-5-methylhexane A mixture of 10 mmole of lithium diisopropylamide (LDA), formed from n-butyllithium and diisopropylamine, in 10 mL of tetrahydrofuran was cooled to −78° C. Then 2 g of α-isopropyl-3,4-dimethoxybenzyl nitrile was added to the mixture. The reaction mixture was stirred at −78° C. for 20 minutes, 0.78 mL of epibromohydrin was added and stirring was continued for an additional two hours. The reaction mixture was then added to aqueous hydrochloric acid, the aqueous solution was extracted with ether and the ether extracts were combined. The combined extracts were dried over magnesium sulfate, filtered and the organic solvent was removed from the filtrate to provide 2.66 g of an oil which was used immediately in Step (b), below.

Step (b): Preparation of Title Mixture of Racemates

To a solution of 1.77 g of N-methyl-3,4-dimethoxyphenethyl amine in 15 mL of ethanol at room temperature, there was added 2.66 g of the product of Example 1, Step (a), with stirring. The reaction mixture was then heated to about 75° C. for 6 hours. The solvent was removed in vacuo and the reaction products purified using chromatography over silica gel eluting with ethanol/chloroform/ammonium hydroxide. Progress of the chromatographic separation was monitored by thin layer chromatography [silica, ethanol (4%)/chloroform (95%), tri-ethylamine (1%)]. Chromatographic separation (TLC) provided 307 mg of Product A, ($R_f$ of about 0.35) and 374 mg of product B ($R_f$ about 0.3). In addition, 1.2 g of a mixture of Product A and Product B was obtained. Each of Product A and Product B constitute a racemate of the structure above.

| | Combustion Analysis Results: | |
|---|---|---|
| | Calculated: | Found |
| | Product A: | |
| C | 68.91% | 68.50% |
| H | 8.14% | 7.88% |
| N | 5.95% | 5.60% |
| | Product B: | |
| C | 68.91% | 67.16% |
| H | 8.14% | 7.87% |
| N | 5.95% | 5.69% |

BIOLOGICAL EVALUATION

Assay A: Suppression of Murine Mitogen-Stimulated Proliferation

It is known that lymphocyte activation can be polyclonally stimulated by plant lectins and other mitogenic substances that induce blast transformation and mitosis. The plant lectin concanavalin A (conA) preferentially induces activation and proliferation of T lymphocytes. Exposure of T cells to conA results in polyclonal T cell activation, and this response can be used to determine the in vitro index of immunomodulatory effects of test compounds on pan-T cell activation. Spleen cells were harvested aseptically from female Balb/c mice, and cells were extruded by compression in phosphate buffered saline (pH 7.0). Cells were pelleted by centrifugation (300×g/5 min), and erythyrocytes were lysed by resuspension of the spleen cells in a hypotonic solution (5 mL per spleen) containing 0.14M $NH_4Cl$ and 0.017M Tris base, pH 7.2, and incubated for 5 min. An equal volume of freshly prepared medium [Iscove's modified Dubecoo's medium containing 2 mM L-glutamine, 5% heat inactivated (56° C./45 min) fetal bovine serum and 40 μM 2-mercaptoethanol] was added to stop cell lysis. The remaining cells were pelleted, resuspended in medium, filtered through a cotton plug to remove debris, and the leukocytes were then counted. Leukocytes ($10^5$ cells per 100 μl per well) were incubated at 37° C. in a 95%-air/6%-$CO_2$ atmosphere in 96-well microtiter plates for 3 days. At the start of culture conA (1 ug/ml, SIGMA Chemical Co., St. Louis, Mo.) alone or in combination with test compound (0.0001–60 μM final) or vehicle control (0.6% DMSO or ethanol). All test compounds were dissolved in 95% ethanol or 100% DMSO, and subsequent dilutions were prepared in media. Inhibition of conA-stimulated T cell proliferation was measured using a colorimetric indicator of cell growth and proliferation, MTT [3-(4,5-dimethylthiazol-2-yl)-2 diphenyltetrazolium bromide; 100 μl of a 1 mg/ml solution per well, SIGMA] [Mosmann, T., 1988. J. Immunol. Methods 65, 55–63.] Cells were loaded with MTT dye at 37° C. for 4 hours; media supernatants were then aspirated from the cell pellets. MTT loaded cells were solubilized in isopropanol (150 μl per well). Light absorbance was measured at a test wavelength of 570 nM and a reference wavelength of 650 nM using a spectrophotometer. $EC_{50}$ values for immunosuppressive compounds were estimated by four parameter logistical regression analysis of the optical density data [Delean, A., Munson, P. J. and D. Robard, 1978. Am. J. Physiol. 235:397]. Results are shown in Table I.

Assay B: Cell Viability

Measurement of drug-induced cellular cytotoxicity was determined after 48 hours of cell culture with and without conA and with and without test compound or vehicle control. All cell preparations and assay conditions were identical to those described in Assay A. A fluorescence based assay was used to measure cell viability using the carboxyfluorescein derivative 2'-7'-bis-carboxyethyl-5 (6)-carboxyfluorecein (BCECF) as a vital dye [Leeder, J. S., Dosch, H. M., Harper, P. A., Lam, P. and S. P. Spielberg, 1989. Anal. Biochem. 177, 364–372]. The membrane permeant, nonfluorescent ester derivitive, BCECF-AM (100 μl of a 2 ug/ml solution in phosphate buffered saline, pH 7.0, Molecular Probes, Eugene, OR) was added to each cell culture and incubated at 37° C. for 30 min. BCECF-AM penetrates the cell membrane and is then cleaved by cytoplasmic esterases to yield the fluorescent form BCECF. Aliquots of resuspended, dye-loaded leukocyte suspensions (25 μl) were transferred to a 96-well unidirectional vacuum filtration plate (Baxter Healthcare, Inc., Pandex Division, Chicago, ILL.) containing 20 μl of a 0.25% (w/v) suspension of inert, 3.3 μM polystyrene beads. The cells were washed and concentrated on the well membrane under low vacuum, and cell associated fluorescence was measured by front surface fluorometry (485/535 nM) in the Screen Machine (Baxter) using an automated protocol. Probit analysis was used to determine viability as a percentage of relative fluorescence units (RFU) compared to control (cells and medium). The dose of test compound that induced at least 50% cellular toxicity, i.e., a 50% reduction in RFU compared to unstimulated control cells, was recorded. Results are shown in Table I.

TABLE I

| Immunosuppressant Evaluation of Compounds of the Invention | | |
|---|---|---|
| Compound Example # (n = 2) | Assay A $EC_{50}$ (μM) | Assay B 50% TD (μM) |
| 1-A | 12.90 ± 5.75 | 60 |
| 1-B | 17.90 ± 8.16 | 60 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered to a mammalian subject, such as a human subject, by any suitable route, preferably in the form of a pharmaceutical composition adapted to such a route, and in a dose effective for the treatment intended. Therapeutically-effective doses of the compounds of the present invention required to prevent or arrest the progress of the medical condition are readily ascertained by one of ordinary skill in the art. The compounds and composition may, for example, be administered by various routes including oral, nasal, topical, buccal and sublingual, or by parenteral administration such as subcutaneous, intramuscular, intravenous and intradermal routes.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of Formula II:

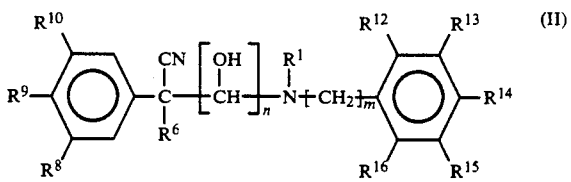

wherein each of m and n is a number independently selected from one to six, inclusive; wherein $R^1$ is selected from hydrido, alkyl, hydroxyalkyl, cycloalkyl, cycloalkylalkyl, alkoxyalkyl, alkenyl and alkynyl;

wherein each of $R^8$, $R^9$, $R^{10}$ and $R^{12}$ through $R^{16}$ is independently selected from hydrido, hydroxy, alkyl, hydroxyalkyl, cycloalkyl, cycloalkylalkyl, cycloalkyloxy, alkoxy, phenoxy, benzyloxy, and radicals of the formulae:

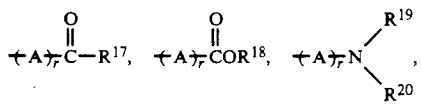

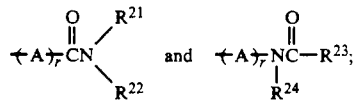

wherein A is a spacer group independently selected from one or more groups of the formulae

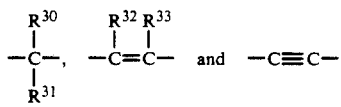

wherein each of $R^{30}$ and $R^{31}$ is independently selected from hydrido, alkyl, cycloalkyl, phenyl, benzyl, hydroxy, hydroxyalkyl, alkoxy, phenoxy, alkoxyalkyl, benzyloxy, cyano, alkanoyl,

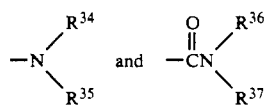

wherein each of $R^{34}$, $R^{35}$, $R^{36}$ and $R^{37}$ is independently selected from hydrido, alkyl and phenyl; wherein $R^{30}$ and $R^{31}$ further may be taken together to form oxo or exomethylene; wherein each of $R^{32}$ and $R^{33}$ is independently selected from hydrido, alkyl, hydroxyalkyl and alkoxyalkyl;
wherein each of $R^{17}$, $R^{18}$, $R^{19}$, $R^{20}$, $R^{21}$, $R^{22}$, $R^{23}$ and $R^{24}$ is independently selected from hydrido, alkyl, cycloalkyl, cycloalkylalkyl and phenalkyl;
wherein each r is a number independently selected from zero to four, inclusive;
wherein $R^6$ is selected from hydrido, alkyl, hydroxyalkyl, cycloalkyl, cycloalkylalkyl, benzyl, alkenyl and alkynyl; and
wherein any of the foregoing A and $R^1$, $R^6$, $R^8$, $R^9$, $R^{10}$, $R^{12}$ through $R^{24}$ and $R^{30}$ through $R^{37}$ groups having a substitutable position may be substituted by one or more groups independently selected from alkyl, alkenyl, alkynyl, hydroxy, benzyl, hydroxyalkyl, alkoxyalkyl, cycloalkyl, cycloalkylalkyl and phenyl;
or a tautomer thereof or a pharmaceutically-acceptable salt thereof.

2. Compound of claim 1 wherein m is one or two; wherein n is a number selected from one to five, inclusive;
wherein $R^1$ is selected from hydrido, alkyl, hydroxyalkyl, alkoxyalkyl, alkenyl and alkynyl;
wherein each of $R^8$, $R^9$, $R^{10}$ and $R^{12}$ through $R^{16}$ is independently selected from hydrido, hydroxy, alkyl, hydroxyalkyl, alkoxy, and radicals of the formulae

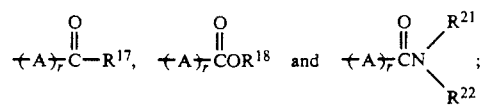

wherein A is a spacer group independently selected from one or more groups of the formulae

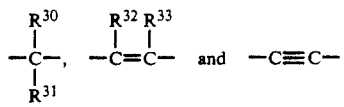

wherein each of $R^{30}$ and $R^{31}$ is independently selected from hydrido, alkyl, cycloalkyl, phenyl, benzyl, hydroxy, hydroxyalkyl, alkoxy and alkoxy and alkoxyalkyl;
wherein each of $R^{32}$ and $R^{33}$ is independently selected from hydrido, alkyl, hydroxyalkyl and alkoxyalkyl;
wherein each of $R^{17}$, $R^{18}$, $R^{21}$ and $R^{22}$ is independently selected from hydrido and alkyl;
wherein each r is a number independently selected from zero to four, inclusive;
wherein $R^6$ is selected from hydrido, alkyl, hydroxyalkyl, cycloalkyl, cycloalkylalkyl, benzyl, alkenyl and alkynyl; and
wherein any of the foregoing A and $R^1$, $R^6$, $R^8$, $R^9$, $R^{10}$, $R^{12}$ through $R^{18}$, $R^{21}$, $R^{22}$ and $R^{30}$ through $R^{33}$ groups having a substitutable position may be substituted by one or more groups independently selected from alkyl, alkenyl, alkynyl, hydroxy, hydroxyalkyl and alkoxyalkyl;
or a tautomer thereof or a pharmaceutically-acceptable salt thereof.

3. Compound of claim 2 wherein m is one or two; wherein n is a number selected from one to five, inclusive; wherein $R^1$ is selected from hydrido, alkyl, hydroxyalkyl, cycloalkyl, cycloalkylalkyl, alkoxyalkyl, alkenyl and alkynyl; wherein $R^6$ is selected from loweralkyl; wherein each of $R^8$, $R^9$, $R^{10}$ and $R^{12}$ through $R^{16}$ is independently selected from hydrido, hydroxy, alkyl, hydroxyalkyl, alkoxy, alkenyl, alkynyl, alkylcarbonyl, alkoxycarbonyl, alkylcarbonylalkenyl, alkylaminocarbonyl and alkoxyalkyl; or a tautomer thereof or a pharmaceutically-acceptable salt thereof.

4. Compound of claim 3 selected from compounds and their pharmaceutically-acceptable salts of the group consisting of
methyl 2-[2-[[2-hydroxy-4-cyano-4-(3,4-dimethoxyphenyl)-5-methylhexyl]methylamino]ethyl]-4,5-dimethoxybenzoate;
ethyl 2-[2-[[2-hydroxy-4-cyano-4-(3,4-dimethoxyphenyl)-5-methylhexyl]methylamino]ethyl]-4,5-dimethoxybenzoate;
n-propyl 2-[2-[[2-hydroxy-4-cyano-4-(3,4-dimethoxyphenyl)-5-methylhexyl]methylamino]ethyl]-4,5-dimethoxybenzoate;
n-butyl 2-[2-[[2-hydroxy-4-cyano-4-(3,4-dimethoxyphenyl)-5-methylhexyl]methylamino]ethyl]-4,5-dimethoxybenzoate;
n-hexyl 2-[2-[[2-hydroxy-4-cyano-4-(3,4-dimethoxyphenyl)-5-methylhexyl]methylamino]ethyl]-4,5-dimethoxybenzoate;
2-[2-[[2-hydroxy-4-cyano-4-(3,4-dimethoxyphenyl)-5-methylhexyl]methylamino]ethyl]-N-(1,1-dimethylethyl)-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-methyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-ethyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-propyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-butyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-pentyl-4,5-dimethoxybenzamide;

2-[2-[[2-hydroxy-4-cyano-4-(3,4-dimethoxyphenyl)-5-methylhexyl]methylamino]ethyl]-N-ethyl-4,5-dimethoxybenzamide;

2-[2-[[2-hydroxy-4-cyano-4-(3,4-dimethoxyphenyl)-5-methylhexyl]methylamino]ethyl]-N-methyl-4,5-dimethoxybenzamide;

2-[2-[[2-hydroxy-4-cyano-4-(3,4-dimethoxyphenyl)-5-methylhexyl]methylamino]ethyl]-N-propyl-4,5-dimethoxybenzamide;

2-[2-[[2-hydroxy-4-cyano-4-(3,4-dimethoxyphenyl)-5-methylhexyl]methylamino]ethyl]-N-butyl-4,5-dimethoxybenzamide;

2-[2-[[2-hydroxy-4-cyano-4-(3,4-dimethoxyphenyl)-5-methylhexyl]methylamino]ethyl]-N-pentyl-4,5-dimethoxybenzamide;

α-[3-[[2-(4,5-dimethoxy-2-methylphenyl)ethyl]methylamino]-2-hydroxypropyl]-3,4-dimethoxy-α-(1-methylethyl)benzeneacetonitrile;

α-[3-[[2-(4,5-dimethoxy-2-ethylphenyl)ethyl]methylamino]-2-hydroxypropyl]-3,4-dimethoxy-α-(1-methylethyl)benzeneacetonitrile;

α-[3-[[2-(4,5-dimethoxy-2-propylphenyl)ethyl]methylamino]-2-hydroxypropyl]-3,4-dimethoxy-α-(1-methylethyl)benzeneacetonitrile;

α-[3-[[2-(4,5-dimethoxy-2-butylphenyl)ethyl]methylamino]-2-hydroxypropyl]-3,4-dimethoxy-α-(1-methylethyl)benzeneacetonitrile;

α-[3-[[2-(4,5-dimethoxy-2-pentylphenyl)ethyl]methylamino]-2-hydroxypropyl]-3,4-dimethoxy-α-(1-methylethyl)benzeneacetonitrile;

α-[3-[[2-(4,5-dimethoxy-2-methylphenyl)ethyl]methylamino]-2-hydroxypropyl]-3,4,5-trimethoxy-α-(1-methylethyl)benzeneacetonitrile;

α-[3-[[2-(4,5-dimethoxy-2-ethylphenyl)ethyl]methylamino]-2-hydroxypropyl]-3,4,5-trimethoxy-α-(1-methylethyl)benzeneacetonitrile;

α-[3-[[2-(4,5-dimethoxy-2-propylphenyl)ethyl]methylamino]-2-hydroxypropyl]-3,4,5-trimethoxy-α-(1-methylethyl)benzeneacetonitrile;

α-[3-[[2-(4,5-dimethoxy-2-butylphenyl)ethyl]methylamino]-2-hydroxypropyl]-3,4,5-trimethoxy-α-(1-methylethyl)benzeneacetonitrile;

α-[3-[[2-(4,5-dimethoxy-2-pentylphenyl)ethyl]methylamino]-2-hydroxypropyl]-3,4,5-trimethoxy-α-(1-methylethyl)benzeneacetonitrile;

α-[3-[[2-[4,5-dimethoxy-2-(3-oxo-1E-butenyl)phenyl]ethyl]-methylamino]2-hydroxypropyl]-3,4-dimethoxy-α-(1-methylethyl)benzeneacetonitrile;

α-[3-[[2-[4,5-dimethoxy-2-(3-oxo-1E-pentenyl)-phenyl]ethyl]-methylamino]2-hydroxypropyl]-3,4-dimethoxy-α-(1-methylethyl)benzeneacetonitrile;

α-[3-[[2-[4,5-dimethoxy-2-(3oxo-1E-butanyl)phenyl]ethyl]-methylamino]2-hydroxypropyl]-3,4-dimethoxy-α-(1-methylethyl)benzeneacetonitrile;

α-[3-[[2-[2-(hydroxymethyl)-4,5-dimethoxyphenyl]ethyl]-methylamino]2-hydroxypropyl]-3,4-dimethoxy-α(1-methylethyl)benzeneacetonitrile; and 1-methylethyl 2-[2-[[2-hydroxy-4-cyano-4-(3,4-dimethoxyphenyl)-5-methylhexyl]methylamino]ethyl]-4,5-dimethoxybenzoate.

5. Compound of claim 4 which is α-[3-[[2-(3,4-dimethoxyphenyl)ethyl]methylamino]-2-hydroxypropyl]-3,4-dimethoxy-α-(1-methylethyl)benzeneacetonitrile or a pharmaceutically-acceptable salt thereof.

6. A composition comprising a therapeutically-effective amount of an immunosuppressive compound and a pharmaceutically acceptable carrier or diluent, said immunosuppressive compound selected from compounds of Formula II:

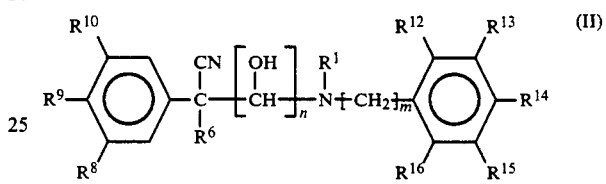

wherein each of m and n is a number independently selected from one to six, inclusive; wherein $R^1$ is selected from hydrido, alkyl, hydroxyalkyl, cycloalkyl, cycloalkylalkyl, alkoxyalkyl, alkenyl and alkynyl;

wherein each of $R^8$, $R^9$, $R^{10}$ and $R^{12}$ through $R^{16}$ is independently selected from hydrido, hydroxy, alkyl, hydroxyalkyl, cycloalkyl, cycloalkylalkyl, cycloalkyloxy, alkoxy, phenoxy, benzyloxy, and radicals of the formulae

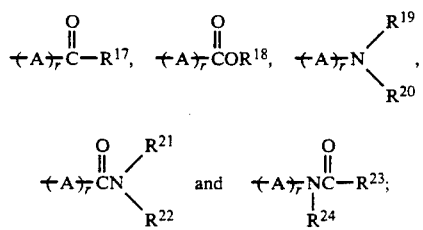

wherein A is a spacer group independently selected from one or more groups of the formulae

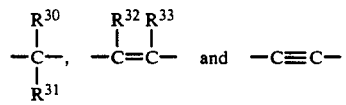

wherein each of $R^{30}$ and $R^{31}$ is independently selected from hydrido, alkyl, cycloalkyl, phenyl, benzyl, hydroxy, hydroxyalkyl, alkoxy, phenoxy, alkoxyalkyl, benzyloxy, cyano, alkanoyl,

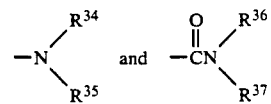

wherein each of $R^{34}$, $R^{35}$, $R^{36}$ and $R^{37}$ is independently selected from hydrido, alkyl and phenyl; wherein $R^{30}$ and $R^{31}$ may further be taken together to form oxo or exomethylene; wherein each of $R^{32}$ and $R^{33}$ is independently selected from hydrido, alkyl, hydroxyalkyl and alkoxyalkyl;

wherein each of $R^{17}$, $R^{18}$, $R^{19}$, $R^{20}$, $R^{21}$, $R^{22}$, $R^{23}$ and $R^{24}$ is independently selected from hydrido, alkyl, cycloalkyl, cycloalkylalkyl and phenalkyl;

wherein each r is a number independently selected from zero to four, inclusive;

wherein $R^6$ is selected from hydrido, alkyl, hydroxyalkyl, cycloalkyl, cycloalkylalkyl, benzyl, alkenyl and alkynyl; and wherein any of the foregoing A and $R^1$, $R^6$, $R^8$, $R^9$, $R^{10}$, $R^{12}$ through $R^{24}$ and $R^{30}$ through $R^{37}$ groups having a substitutable position may be substituted by one or more groups independently selected from alkyl, alkenyl, alkynyl, hydroxy, benzyl, hydroxyalkyl, alkoxyalkyl, cycloalkyl, cycloalkylalkyl and phenyl;

or a tautomer thereof or a pharmaceutically-acceptable salt thereof.

7. The composition of claim 6 wherein m is one or two;
wherein n is a number selected from one to five, inclusive;
wherein $R^1$ is selected from hydrido, alkyl, hydroxyalkyl, alkoxyalkyl, alkenyl and alkynyl;
wherein each of $R^8$, $R^9$, $R^{10}$ and $R^{12}$ through $R^{16}$ is independently selected from hydrido, hydroxy, alkyl, hydroxyalkyl, alkoxy, and radicals of the formulae

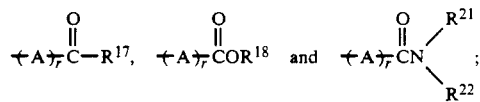

wherein A is a spacer group independently selected from one or more groups of the formulae

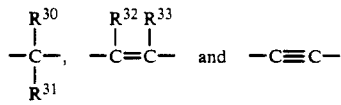

wherein each of $R^{30}$ and $R^{31}$ is independently selected from hydrido, alkyl, cycloalkyl, phenyl, benzyl, hydroxy, hydroxyalkyl, alkoxy and alkoxy and alkoxyalkyl;
wherein each of $R^{32}$ and $R^{33}$ is independently selected from hydrido, alkyl, hydroxyalkyl and alkoxyalkyl;
wherein each of $R^{17}$, $R^{18}$, $R^{21}$ and $R^{22}$ is independently selected from hydrido and alkyl;
wherein each r is a number independently selected from zero to four, inclusive;
wherein $R^6$ is selected from hydrido, alkyl, hydroxyalkyl, cycloalkyl, cycloalkylalkyl, benzyl, alkenyl and alkynyl; and
wherein any of the foregoing A and $R^1$, $R^6$, $R^8$, $R^9$, $R^{10}$, $R^{12}$ through $R^{18}$, $R^{21}$, $R^{22}$ and $R^{30}$ through $R^{33}$ groups having a substitutable position may be substituted by one or more groups independently selected from alkyl, alkenyl, alkynyl, hydroxy, hydroxyalkyl and alkoxyalkyl;

or a tautomer thereof or a pharmaceutically-acceptable salt thereof.

8. The composition of claim 7 wherein m is one or two; wherein n is a number selected from one to five, inclusive; wherein $R^1$ is selected from hydrido, alkyl, hydroxyalkyl, cycloalkyl, cycloalkylalkyl, alkoxyalkyl, alkenyl and alkynyl; wherein $R^6$ is selected from loweralkyl; wherein each of $R^8$, $R^9$, $R^{10}$ and $R^{12}$ through $R^{16}$ is independently selected from hydrido, hydroxy, alkyl, hydroxyalkyl, alkoxy, alkenyl, alkynyl, alkylcarbonyl, alkoxycarbonyl, alkylcarbonylalkenyl, alkylaminocarbonyl and alkoxyalkyl; or a tautomer thereof or a pharmaceutically-acceptable salt thereof.

9. The composition of claim 8 wherein said immunosuppressive compound is selected from compounds and their pharmaceutically-acceptable salts of the group consisting of methyl 2-[2-[[2-hydroxy-4-cyano-4-(3,4-dimethoxyphenyl)-5-methylhexyl]methylamino]ethyl]-4,5-dimethoxybenzoate;

ethyl 2-[2-[[2-hydroxy-4-cyano-4-(3,4-dimethoxyphenyl)-5-methylhexyl]methylamino]ethyl]-4,5-dimethoxybenzoate;

n-propyl 2-[2-[[2-hydroxy-4-cyano-4-(3,4-dimethoxyphenyl)-5-methylhexyl]methylamino]ethyl]-4,5-dimethoxybenzoate;

n-butyl 2-[2-[[2-hydroxy-4-cyano-4-(3,4-dimethoxyphenyl)-5-methylhexyl]methylamino]ethyl]-4,5-dimethoxybenzoate;

n-hexyl 2-[2-[[2-hydroxy-4-cyano-4-(3,4-dimethoxyphenyl)-5-methylhexyl]methylamino]ethyl]-4,5-dimethoxybenzoate;

2-[2-[[2-hydroxy-4-cyano-4-(3,4-dimethoxyphenyl)-5-methylhexyl]methylamino]ethyl]-N-(1,1-dimethylethyl)-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-methyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-ethyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-propyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-butyl-4,5-dimethoxybenzamide;

2-[2-[[2-hydroxy-4-cyano-4-(3,4-dimethoxyphenyl)-5-methylhexyl]methylamino]ethyl]-N-(1,1-dimethylethyl)-N-pentyl-4,5-dimethoxybenzamide;

2-[2-[[2-hydroxy-4-cyano-4-(3,4-dimethoxyphenyl)-5-methylhexyl]methylamino]ethyl]-N-ethyl-4,5-dimethoxybenzamide;

2-[2-[[2-hydroxy-4-cyano-4-(3,4-dimethoxyphenyl)-5-methylhexyl]methylamino]ethyl]-N-methyl-4,5-dimethoxybenzamide;

2-[2-[[2-hydroxy-4-cyano-4-(3,4-dimethoxyphenyl)-5-methylhexyl]methylamino]ethyl]-N-propyl-4,5-dimethoxybenzamide;

2-[2-[[2-hydroxy-4-cyano-4-(3,4-dimethoxyphenyl)-5-methylhexyl]methylamino]ethyl]-N-butyl-4,5-dimethoxybenzamide;

2-[2-[[2-hydroxy-4-cyano-4-(3,4-dimethoxyphenyl)-5-methylhexyl]methylamino]ethyl]-N-pentyl-4,5-dimethoxybenzamide;

α-[3-[[2-(4,5-dimethoxy-2-methylphenyl)ethyl]methylamino]-2-hydroxypropyl]-3,4-dimethoxy-α-(1-methylethyl)benzeneacetonitrile;

α-[3-[[2-(4,5-dimethoxy-2-ethylphenyl)ethyl]methylamino]-2-hydroxypropyl]-3,4-dimethoxy-α-(1-methylethyl)benzeneacetonitrile;

α-[3-[[2-(4,5-dimethoxy-2-propylphenyl)ethyl]methylamino]-2-hydroxypropyl]-3,4-dimethoxy-α-(1-methylethyl)benzeneacetonitrile;

α-[3-[[2-(4,5-dimethoxy-2-butyphenyl)ethyl]methylamino]-2-hydroxypropyl]-3,4-dimethoxy-α-(1-methylethyl)benzeneacetonitrile;

α-[3-[[2-(4,5-dimethoxy-2-pentylphenyl)ethyl]methylamino]-2-hydroxypropyl]-3,4-dimethoxy-α-(1-methylethyl)benzeneacetonitrile;

α-[3-[[2-(4,5-dimethoxy-2-methylphenyl)ethyl]methylamino]-2-hydroxypropyl]-3,4,5-trimethoxy-α-(1-methylethyl)benzeneacetonitrile;

α-[3-[[2-(4,5-dimethoxy-2-ethylphenyl)ethyl]methylamino]-2-hydroxypropyl]-3,4,5-trimethoxy-α-(1-methylethyl)benzeneacetonitrile;

α-[3-[[2-(4,5-dimethoxy-2-propylphenyl)ethyl]methylamino]-2-hydroxypropyl]-3,4,5-trimethoxy-α-(1-methylethyl)benzeneacetonitrile;

α-[3-[[2-(4,5-dimethoxy-2-butylphenyl)ethyl]methylamino]-2-hydroxypropyl]-3,4,5-trimethoxy-α-(1-methylethyl)benzeneacetonitrile;

α-[3-[[2-(4,5-dimethoxy-2-pentylphenyl)ethyl]methylamino]-2-hydroxypropyl]-3,4,5-trimethoxy-α-(1-methylethyl)benzeneacetonitrile;

α-[3-[[2-[4,5-dimethoxy-2-(3-oxo-1E-butenyl)phenyl]ethyl]methylamino]2-hydroxypropyl]-3,4-dimethoxy-α-(1-methylethyl)benzeneacetonitrile;

α-[3-[[2-[4,5-dimethoxy-2-(3-oxo-1E-pentenyl)phenyl]ethyl]methylamino]2-hydroxypropyl]-3,4-dimethoxy-α-(1-methylethyl)benzeneacetonitrile;

α-[3-[[2-[4,5-dimethoxy-2-(3-oxo-1E-butanyl)phenyl]ethyl]methylamino]2-hydroxypropyl]-3,4-dimethoxy-α-(1-methylethyl)benzeneacetonitrile;

α-[3-[[2-[2-(hydroxymethyl)-4,5-dimethoxyphenyl]ethyl]methylamino]2-hydroxypropyl]-3,4-dimethoxy-α-(1-methylethyl)benzeneacetonitrile; and 1-methylethyl 2-[2-[[2-hydroxy-4-cyano-4-(3,4-dimethoxyphenyl)-5-methylhexyl]methylamino]ethyl]-4,5-dimethoxybenzoate.

10. The composition of claim 9 wherein said immunosuppressive compound is α-[3-[[2-(3,4-dimethoxyphenyl)ethyl]methylamino]-2-hydroxypropyl]-3,4-dimethoxy-α-(1-methylethyl)benzeneacetonitrile or a pharmaceutically-acceptable salt thereof.

* * * * *